(12) United States Patent
Yu et al.

(10) Patent No.: US 7,491,706 B2
(45) Date of Patent: Feb. 17, 2009

(54) ARTIFICIAL CPG SINGLE-STRANDED OLIGODEOXYNUCLEOTIDE AND ANTIVIRAL USE THEREOF

(75) Inventors: Yongli Yu, Changchun (CN); Liying Wang, Changchun (CN)

(73) Assignee: Changchun Huapu Biotechnology Co., Ltd., Changchun, Jilin (CN)

( * ) Notice: Subject to any disclaimer, the term of this patent is extended or adjusted under 35 U.S.C. 154(b) by 172 days.

(21) Appl. No.: 10/565,718

(22) PCT Filed: Jul. 26, 2004

(86) PCT No.: PCT/CN2004/000863

§ 371 (c)(1),
(2), (4) Date: Aug. 28, 2006

(87) PCT Pub. No.: WO2005/014611

PCT Pub. Date: Feb. 17, 2005

(65) Prior Publication Data

US 2007/0155683 A1    Jul. 5, 2007

(30) Foreign Application Priority Data

Jul. 25, 2003   (CN)   ................. 03 1 46157
Sep. 5, 2003    (CN)   ................. 03 1 56224

(51) Int. Cl.
*A01N 43/04*   (2006.01)
*A01N 37/18*   (2006.01)

(52) U.S. Cl. ................. 514/44; 514/2; 424/180.1; 424/185.1; 424/192.1; 424/193.1; 435/91.1; 435/91.5; 536/23.1; 536/23.4; 536/23.5; 536/23.52; 536/25.3

(58) Field of Classification Search ............ None
See application file for complete search history.

(56) References Cited

U.S. PATENT DOCUMENTS 6,218,371 B1 *   4/2001   Krieg et al. ................. 514/44

FOREIGN PATENT DOCUMENTS

| CN | 031408214  | 5/2004 |
| CN | 03119840.6 | 9/2004 |
| CN | 03119841.4 | 9/2004 |

OTHER PUBLICATIONS

Sheehan et al (2003) Nucleic Acids Research. 31(14): 4109-4118.*
Peng, X et al. (2002) "Synthesis of single-stranded DNA probe using technique of primer length-asymmetric PCR" *Chin. J. Lab Diagn.* 6:206-208.
Li, J. et al (2002) "The effect of transgenic expression of porcine interleukin-6 gene and cpg sequences on immune responses of mice inoculated with the gene vaccine of taenia solium of pig" *High Tech Communications*, pp. 26-30.
Yuan, Y-F. et al. (2002) "The roles of dna methelytion in human neoplasms" *Chinese Journal of Cancer*, 21:1267-1277.

* cited by examiner

*Primary Examiner*—Bruce Campell
*Assistant Examiner*—Michelle Horning
(74) *Attorney, Agent, or Firm*—Knobbe, Martens, Olson & Bear, LLP

(57) ABSTRACT

The present invention provides a series of artificial CpG-containing single-stranded oligodeoxynucleotides (ODNs), each of which is consisted of single-stranded oligodeoxynucleotide DNA molecule containing one or more CpG(s), wherein said ODNs can stimulate human peripheral blood mononuclear cell (PBMC) to produce antiviral substances. These ODNs can protect the cells against the attack from virus, wherein said virus is preferably selected from the group consisted of influenza virus and single-stranded positive strand RNA virus such as SARS virus, hepatitis C virus, dengue virus and Japanese encephalitis virus. Moreover, the antiviral use of artificial CpG ODNs and its use for treating and preventing viral infection are also provided.

14 Claims, 1 Drawing Sheet

```
                        SEQUENCE LISTING

<160> NUMBER OF SEQ ID NOS: 5

<210> SEQ ID NO 1
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 1
tcgtcgggtg cgacgtcgca gggggg                                          26

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 2
tcgtcgtttc gtcgttgggg                                                 20

<210> SEQ ID NO 3
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 3
tcgacgttcg tcgttcgtcg ttc                                             23
```

```
<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 4
tcggggacga tcgtcggggg g                                              21

<210> SEQ ID NO 5
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 5
ggatcgatcg atcgatgggg gg                                             22
```

ARTIFICIAL CPG SINGLE-STRANDED OLIGODEOXYNUCLEOTIDE AND ANTIVIRAL USE THEREOF

FIELD OF THE INVENTION

This invention relates to a serial of artificial CpG-containing single-stranded oligodeoxynucleotides (ODNs) having antiviral function. In particularly, the invention relates to artificial CpG-containing single-stranded oligodeoxynucleotides, which are effective for the prevention and treatment of infectious diseases caused by single-stranded positive strand RNA virus such as SARS virus, hepatitis C virus, dengue virus and Japanese encephalitis virus and by influenza virus. The present invention further relates to a method of preventing or treating infectious diseases caused by viruses, in particularly single-stranded positive strand RNA virus such as SARS virus, hepatitis C virus, dengue virus and Japanese encephalitis virus, and by influenza virus, which method employs the artificial CpG-containing single-stranded oligodeoxynucleotides according to the present invention.

DESCRIPTION OF THE RELATED ART

Recently, studies have demonstrated that many bacterial and viral DNAs possessing CpG structure represent a danger signal for human immune system and are capable of activating a variety of immune cells to initiate the defense mechanism of body against the bacteria and virus. CpG is a dinucleotide formed by the connection of cytosine and guanine through phosphoric acid, wherein C denotes cytosine, G denotes guanine and p denotes phosphoric acid. Further studies indicate that artificial single-stranded oligodeoxynucleotide DNA containing one or more CpG(s) (CpG ODN) can also show potent immunoenhancing and immunoregulatory function, activate a variety of immune cells to start the defense mechanism of body against virus, and exhibit a promising potential for clinic application.

Administration of CpG ODN to mice and guinea pigs through vagina can improve the ability of the mice and guinea pigs to protect against the challenge with lethal dose of HSV-2 virus (Pyles, R. B. et al. 2002 *Journal of Virology*, 76(22):11387-11396). Administration of CpG ODN to mice can reduce the virus load of respiratory syncytial virus (RSV) (Cho, J. Y., et al. 2001 *J Allergy. Clin. Immunol.*, 108(5):697-702). Treatment of Friend virus (a murine leucovirus)-infected mice with CpG ODN significantly reduces the virus burden in blood of the mice (Olbrich, A. R. M. et al. 2002 *Journal of Virology*, 76(22):11397-11404). Normal C57BL/6 mice are pretreated with CpG ODN by intravenous injection two days before the intravenous challenge of normal lethal dose of herpes simplex virus (HSV-2), and as a result CpG ODN significantly reduces the viral titre in vaginal secrete of the mice and stimulates the genital tract to produce protective cytokines such as IFN-γ, IL-12 and IL-18 rapidly (Harandi, A. M., et al. 2003 *Journal of Virology*, 77(2):953).

Influenza virus is a pathogen that causes human influenza. During 1918-1919, about twenty million people died of influenza (Patterson, K. D. & Pyle, G. F. 1991 *Bull. Hist. Med.*, 65:4-213). The severity and uncontrollability of influenza virus correlates with its following characteristics closely:

(1) airborne;

(2) antigenic drift (Parvin, J. D. & Moscona, A. 1986 *J Virol.*, 59:377-383; Webster, R. G. 1982 *Nature*, 296:115-121);

(3) production of new variants by RNA cross-recombination between different influenza virus strains in a same infected cell (Webster, R. G. 1982 *Microbiol. Rev.*, 56:152-179).

Vaccination and antiviral drugs are two main measures for the prevention and treatment of influenza virus (Bridges, C. B. et al. 2001 *Morbid. Mortal., Wkly. Rep.*, 50:1-44). The fact, however, proves that neither of above two methods can control the prevalence of influenza effectively (Webby, R. J. & Webster, R. G. 2001 *Philos. Trans. R. Soc., London*, 356:1817-1828). The protection percentage of short-term (half a year) vaccination in susceptible population is about 39% (Fukuda, K. & Cox, N. J. 1999 *Morbid. Mortal., Wkly. Rep.*, 48:1-28; Castle, S. C. 2000 *Clin. Infect. Dis.*, 31:578-585). Because the antigens (haemagglutinin and neural amidase) of influenza virus are everchanging, current vaccines are reconstructed almost every year accordingly. Due to having relatively large side effect and continual appearance of new drug-resistant influenza virus strains, some approved antiviral drugs for influenza are not satisfied in terms of efficacy (Luscher-Mattli, M. 2000 *Arch. Virol.*, 145:2233-2248).

Infectious atypical pneumonia is an infectious human respiratory disease caused by SARS virus and may induce severe acute respiratory syndrome (SARS) with a mortality of 4-12%. The pathogen of infectious atypical pneumonia is a variant of coronavirus, i.e. SARS virus, and belongs to enveloped single-stranded positive strand RNA virus (Drosten, C. 2003 *The New England Journal of Medicine*, 348:19; Rota, P. A., et al. 2003 *Science*, 300 (Issue 5624):1394-1399). Hepatitis C virus, the pathogen of hepatitis C, is also an enveloped single-stranded positive strand RNA virus (Lindenbach, B. D. & Rice, C. M. 2001 In *Fields virology*, D. M. Knipe & P. M. Howley (ed.), 1:991-1041, Lippincott/The Williams and Wilkins Co., Philadelphia, Pa.). Hepatitis C virus falls into flaviviridae. Another two viruses of flaviviridae, dengue virus (Wang, W.-K., et al. 2002 *Journal of Virology*, 76(9):4662-4665) and Japanese encephalitis virus (Yun, S.-I. 2003 *Journal of Virology*, 77(11):6450-6465), are also enveloped single-stranded positive strand RNA viruses. At present, no effective therapy is available for the treatment of infectious human respiratory diseases and severe acute respiratory syndrome caused by SARS virus. The therapeutic effects of some antiviral drugs for infectious diseases caused by hepatitis C virus, dengue virus and Japanese encephalitis virus are still not satisfactory.

SUMMARY OF THE INVENTION

The first objective of the invention is to provide an artificial single-stranded oligodeoxynucleotide which contains CpG (s), in particularly an artificial CpG-containing single-stranded oligodeoxynucleotide which can stimulate human peripheral blood mononuclear cell (PBMC) to produce antiviral substances, wherein said virus includes single-stranded positive strand RNA virus and influenza virus. The artificial CpG-containing single-stranded oligodeoxynucleotide is consisted of single-stranded oligonucleotide DNA molecule, which contains one or more CpG(s) and has a non-sulfurized, partially sulfurized or completely sulfurized phosphodiester bond. Preferably, the artificial CpG-containing single-stranded oligodeoxynucleotide according to present invention has a sequence as defined by SEQ ID NO: 1, SEQ ID NO: 2, SEQ ID NO: 3, SEQ ID NO: 4 or SEQ ID NO: 5.

The second objective of the invention is to provide an antiviral use of the artificial CpG-containing single-stranded oligodeoxynucleotide according to present invention, in particularly single-stranded positive strand RNA virus such as SARS virus, hepatitis C virus, dengue virus and Japanese encephalitis virus as well as influenza virus.

The third objective of the invention is to provide a use of the artificial CpG-containing single-stranded oligodeoxynucleotide according to present invention for preventing and treating diseases caused by virus, in particularly infectious diseases caused by single-stranded positive strand RNA virus such as SARS virus, hepatitis C virus, dengue virus and Japanese encephalitis virus and by influenza virus.

The fourth objective of the invention is to provide a method of preventing and treating diseases caused by virus with the artificial CpG-containing single-stranded oligodeoxynucleotide according to present invention, wherein said diseases are particularly infectious diseases caused by single-stranded positive strand RNA virus such as SARS virus, hepatitis C virus, dengue virus and Japanese encephalitis virus and by influenza virus.

In the context of this invention, unless indicated otherwise, the terms used herein possess the meanings generally understood by those skilled in the art. In particularly, the following terms have the following meanings:

Preferably, the CpG-containing single-stranded oligodeoxynucleotide according to present invention has a sequence as defined by the following sequences:

```
                                          SEQ ID NO: 1
    DVAX-1: 5'-TCgTCgggTgCgACgTCgCAgggggg-3'

SEQ ID NO: 2
    DVAX-3: 5'-TCgTCgTTTCgTCgTTgggg-3'

SEQ ID NO: 3
    DVAX-4: 5'-TCgACgTTCgTCgTTCgTCgTTC-3'

SEQ ID NO: 4
    DVAX-5: 5'-TCggggACgATCgTCgggggg-3'

SEQ ID NO: 5
    DVAX-6: 5'-ggATCgATCgATCgATgggggg-3',
``` which has a non-sulfurized, partially sulfurized or completely sulfurized phosphodiester bond.

The CpG single-stranded oligodeoxynucleotide according to the present invention may be synthesized by known methods, for example solid phase phosphoramidite triester method. The following examples illustrate a process to produce the CpG-containing single-stranded oligodeoxynucleotide according to the invention.

In preventing and treating human infectious diseases caused by single-stranded positive strand RNA virus such as SARS virus, hepatitis C virus, dengue virus and Japanese encephalitis virus, the dosage of the CpG-containing single-stranded oligodeoxynucleotide for a single administration is 1-5000 μg.

The artificial CpG-containing single-stranded oligodeoxynucleotide according to present invention can be used alone or in combination with other antiviral drugs or vaccines, wherein said antiviral drugs or vaccines used for the prevention and treatment of infectious diseases caused by virus are covalently coupled with the oligodeoxynucleotide and wherein said virus is preferably selected from single-stranded positive strand RNA virus such as SARS virus, hepatitis C virus, dengue virus and Japanese encephalitis virus.

The administration pathway of the oligodeoxynucleotide includes conventional routes such as mucous membrane (including mucous membranes of respiratory tract, digestive tract and genitourinary tract), surface administration, eye drip, subcutaneous injection, intramuscular injection, enterogastric administration, intraperitoneal administration, intravenous injection.

In addition, it should be noted that based on the disclosure of the description, other aspects of the invention possessing substantive features and their inventive beneficial effects will be obvious for an ordinary person skilled in the art.

DETAILED DESCRIPTION OF THE PREFERRED EMBODIMENT

Figure 1:
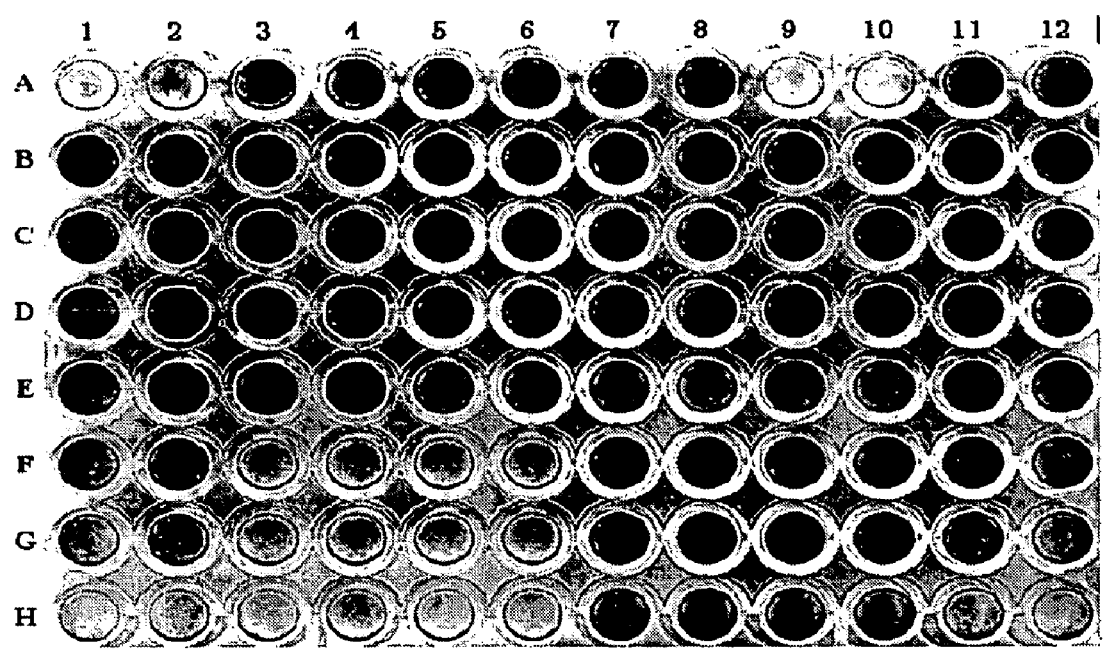
FIG. 1 illustrates that the culture supernatant of human peripheral blood mononuclear cell stimulated by the artificial CpG-containing single-stranded oligodeoxynucleotide according to present invention protects Vero cells from the attack of influenza virus.

The present invention will be further described in detail in conjunction with the following Preparation Examples and Biological Examples. It should be understood that these examples are only for the purpose of illustrating the invention rather than limiting the scope of the invention in any way.

As used in the following examples, processes and methods not described in detail are conventional methods well known in the art. For example, solid phase phosphoramidite triester method is employed in synthetic process. As used in the following examples, the sources, trade names and/or compositions (if necessary) of the agents used herein are described only one time and not repeated for the same agents thereafter for the purpose of conciseness.

EXAMPLES

Example 1

Production of Artificial CpG-containing Single-stranded Oligodeoxynucleotides

The artificial CpG-containing single-stranded oligodeoxynucleotides ware synthesized by solid phase phosphoramidite triester method, which included the following steps:

1) Deprotection

The protective group, dimethoxytrityl (DMT), in the nucleotide attached to a CPG (Controlled Pore Glass) was removed by trichloroacetic acid (TCA) to obtain a free 5'-hydroxyl group, which was available for the next condensation reaction.

2) Activation

Nucleotide monomers protected by phosphoramidite were mixed with tetrazole (activator) and placed into synthesis column to form a tetrazolyl phosphoramidite reactive intermediate (3'-teminus activated while 5'-teminus still protected by DMT). This intermediate would be condensed with the nucleotides on CPG which had been deprotected.

3) Coupling

The tetrazolyl phosphoramidite reactive intermediate contacted with the nucleotides on CPG which had been deprotected and reacted with its 5'-hydroxyl group, wherein a condensation reaction occurred and the tetrazolyl was removed. In this way, the resulting artificial oligodeoxynucleotide extended forward a base.

4) Blocking

After above condensation reaction, acetylation was generally employed to block unreacted 5'-hydroxyl groups attached to CPG in order to avoid its extension during the next cycle. Typically, the acetylation was accomplished by a mixture of acetic anhydride and N-methylimidazole.

5) Oxidation

During above condensation reaction, the nucleotide monomers were connected with oligodeoxynucleotides attached to CPG by phosphite ester linkage. The phosphite ester linkage was unstable and susceptible to hydrolysis by acid or base. In order to obtain stable oligodeoxynucleotides, the phosphite ester therein was conventionally transformed into phosphate triester with a solution of iodine in tetrahydrofuran.

After above five steps, a deoxynucleotide was attached to the nucleotide on CPG. Similarly, trichloroacetic acid was used to remove the newly formed protective group DMT on 5'-hydroxyl group of deoxynucleotide, and above activation, coupling, blocking and oxidation steps were repeated to obtain a crude product of DNA fragment. After post-synthesis processes such as cleavage of protective group (typically benzoyl for A and C; isobutyryl for G; T unprotected; nitrile ethyl for phosphite), deprotection (by conventional methods such as HAP, PAGE, HPLC, C18, OPC), purification and quantitation, the following oligonucleotide fragments (shown as SEQ ID NO: 1-5) according to present invention which met experimental requirements were obtained:

```
DVAX-1
(SEQ ID NO: 1): 5'-TCgTCgggTgCgACgTCgCAggggggg-3'

DVAX-3
(SEQ ID NO: 2): 5'-TCgTCgTTTCgTCgTTgggg-3'

DVAX-4
(SEQ ID NO: 3): 5'-TCgACgTTCgTCgTTCgTCgTTC-3'

DVAX-5
(SEQ ID NO: 4): 5'-TCggggACgATCgTCgggggg-3'

DVAX-6
(SEQ ID NO: 5): 5'-ggATCgATCgATCgATgggggg-3'.
```

Non-sulfurized CpG single-stranded oligodeoxynucleotides were synthesized by ABI 3900 DNA Synthesizer, while completely sulfurized or partially sulfurized CpG single-stranded oligodeoxynucleotides were synthesized by ABI 394 DNA Synthesizer through a substitution method.

Example 2

Antiviral Activity of Artificial CpG-Containing Single-stranded Oligodeoxynucleotides to Influenza Virus 1. Separation of Human Peripheral Blood Mononuclear Cells (PBMCs)

Human peripheral blood (from two normal blood-donors at Blood Center of Changchun City), which had been treated with heparin for anticoagulation, was added slowly along tube wall to the liquid surface of lymphocytes having a specific gravity of 1.077 ±0.001 which was stratified with Ficoll-Hypaque (purchased from Beijing Dingguo Biotechnology Cooperation Limited). The ratio of the separated liquid and the heparin-anticoagulated peripheral blood was about 2:1.

After horizontal centrifugation at 1,000×g for 15-20 minutes, the liquid in tube was separated into three layers, wherein cells in the cell-rich layer was pipetted and transferred to another tube. Equal volume of Hank's solution was added to the tube, mixed thoroughly, centrifuged at 800-1,000×g for 15 min and supernatant was discarded. The cells were washed by centrifugation of Hank's solution. The Hank's solution (serum-free, without $Ca^{2+}$ and $Mg^{2+}$) was prepared as follows: 8.0 g NaCl, 0.4 g KCl, 0.06 g $Na_2HPO_4.H_2O$, 0.06 g $KH_2PO_4$, 0.35 g $NaHCO_3$, 1.0 g Glucose and 0.02 g phenol red were added to and dissolved in 1000 ml dd$H_2O$. The solution was sterilized under 8 pound for 15 min, stored in refrigerator at 4° C., and adjusted to pH=7.3-7.6 with 7.4% $NaHCO_3$ just before use.

After the last centrifugation, supernatant was discarded and 2 ml of 10% FCS RPMI 1640 complete medium was added to resuspend cells. The RPMI 1640 medium was prepared as follows: 10.4 g RPMI 1640 containing L-glutamine (GIBCOBRL), 2.0 g $NaHCO_3$, 100,000 IU gentamycin were added to 1000 ml $H_2O$ which had been distilled thrice. The solution was sterilized by filtering through 0.22 μm filter membrane under vacuum, and distributed.

A drop of cell suspension was taken, diluted and counted. Total cell counts in four large grids were recorded. Concentration of mononuclear cells (cell count/1 ml cell suspension) =total cell counts in four large grids/4×10$^4$×2 (dilution ratio).

2. Determination of Antiviral Activity of Artificial CpG-Containing Single-Stranded Oligodeoxynucleotides to Influenza Virus Human peripheral blood mononuclear cells was adjusted to a final concentration of $3\times10^6$/ml with IMDM medium supplemented with 10% fetal bovine serum (1000 ml, containing 100,000 IU gentamycin, sterilized by filtering through 0.22 μm filter membrane and distributed). The resultant cell suspension was added to a 12-well culture plate, 2 ml per well. The artificial CpG-containing single-stranded oligodeoxynucleotides were then added (6.25 μg/ml).

DVAX-1 control: an artificial CpG-containing single-stranded oligodeoxynucleotide (5'-TgCTTgggTggCAgCT-gCCAggggggg-3') was added.

Culture control: no artificial CpG-containing single-stranded oligodeoxynucleotide was added and cultivation was conducted at 37° C. in a 5% $CO_2$ incubator for 48 hours. Supernatant was collected and tested for its antiviral activity to influenza virus.

Well-grown Vero cells (ATCC) were adjusted to a final concentration of $3\times10^5$/ml with IMDM supplemented with 5% fetal bovine serum. The cells were seeded into 96-well flat-bottomed plates, 100 μl/well. The supernatants stimulated by CpG-containing single-stranded oligodeoxynucleotides were diluted by tenfold with IMDM supplemented with 5% fetal bovine serum. 100 μl of diluted supernatant was added to each well. Thus, the volume of each well was 200 μl, i.e. 100 μl of cell suspension plus 100 μl of diluted supernatants stimulated by CpG-containing single-stranded oligodeoxynucleotides. An interferon control, an influenza virus control and a normal Vero cell control were arranged. 37° C., 5% $CO_2$ (Changchun Institute of Biological Products) 200 μl, and cultured for further 48-72 hours. The cultivation was stopped when pathological changes occurred in 80-100% cells of virus control wells while the cells in cell control wells grew well. Crystal violet staining was used to assess the extent of cytopathic effect. Culture was discarded. 200 μl of 0.5% crystal violet solution was added to each well and incubated at 37° C. for 15 min. The crystal violet staining solution was washed away with flowing water. 0.5% crystal violet staining solution: 0.5 g crystal violet, 0.85 g NaCl, dissolved in 50 ml anhydrous ether. 3 ml formaldehyde and 47 ml distilled water were added. Pictures were taken to record the results. Samples were applied according to Table 1 and results after crystal violet staining were shown in FIG. 1.

TABLE 1

The table of application of sample for 96-well plate

| | 1 | 2 | 3 | 4 | 5 | 6 | 7 | 8 | 9 | 10 | 11 | 12 |
|---|---|---|---|---|---|---|---|---|---|---|---|---|
| A | Culture control | | IFNα (10 IU/ml) | | IFNα (100 IU/ml) | | IFNα (1000 IU/ml) | | Influenza virus | | Normal Vero cell | |
| B | Normal Vero cell | | IFNα (10 IU/ml) | | IFNα (100 IU/ml) | | IFNα (1000 IU/ml) | | Normal Vero cell | | Normal Vero cell | |
| C | DVAX-1 1:20 dilution 6.25 μ/ml | | DVAX-3 1:20 dilution 6.25 μg/ml | | DVAX-4 1:20 dilution 6.25 μg/ml | | DVAX-5 1:20 dilution 6.25 μg/ml | | DVAX-6 1:20 dilution 6.25 μg/ml | | DVAX-1 1:20 dilution 6.25 μg/ml | |
| D | DVAX-1 1:100 dilution 6.25 μg/ml | | DVAX-3 1:100 dilution 6.25 μg/ml | | DVAX-4 1:100 dilution 6.25 μg/ml | | DVAX-5 1:100 dilution 6.25 μg/ml | | DVAX-6 1:100 dilution 6.25 μg/ml | | DVAX-1 1:100 dilution 6.25 μg/ml | |
| E | DVAX-1 1:500 dilution 6.25 μg/ml | | DVAX-3 1:500 dilution 6.25 μg/ml | | DVAX-4 1:500 dilution 6.25 μg/ml | | DVAX-5 1:500 dilution 6.25 μg/ml | | DVAX-6 1:500 dilution 6.25 μg/ml | | DVAX-1 1:500 dilution 6.25 μg/ml | |
| F | DVAX-3 1:20 dilution 6.25 μg/ml | | DVAX-1 control 1:20 dilution 6.25 μg/ml | | DVAX-1 control 1:20 dilution 6.25 μg/ml | | DVAX-4 1:20 dilution 6.25 μg/ml | | DVAX-5 1:20 dilution 6.25 μg/ml | | DVAX-6 1:20 dilution 6.25 μg/ml | |
| G | DVAX-3 1:100 dilution 6.25 μg/ml | | DVAX-1 control 1:100 dilution 6.25 μg/ml | | DVAX-1 control 1:100 dilution 6.25 μg/ml | | DVAX-4 1:100 dilution 6.25 μg/ml | | DVAX-5 1:100 dilution 6.25 μg/ml | | DVAX-6 1:100 dilution 6.25 μg/ml | |
| H | DVAX-3 1:500 dilution 6.25 μg/ml | | DVAX-1 control 1:500 dilution 6.25 μg/ml | | DVAX-1 control 1:500 dilution 6.25 μg/ml | | DVAX-4 1:500 dilution 6.25 μg/ml | | DVAX-5 1:500 dilution 6.25 μg/ml | | DVAX-6 1:500 dilution 6.25 μg/ml | |

Note:
DVAX-1 control: an artificial CpG-containing single-stranded oligodeoxynucleotide having the following sequence: 5'-TgCTTgggTggCAgCTgCCAgggggg-3'.

Culture control: culture supernatant not added with artificial CpG-containing single-stranded oligodeoxynucleotides.

Normal Vero cell: without addition of influenza virus.

Influenza virus: adding influenza virus, without culture supernatant.

DVAX 1, 3, 4, 5, 6 represent artificial CpG-containing single-stranded oligodeoxynucleotides with names of DVAX 1, 3, 4, 5, 6, respectively.

IFN: IFNα, Changchun Institute of Biological Products.

C, D, E 1-10; F, G, H 3-4: supernatants of induced PBMCs from one blood donor.

C, D, E 11-12; F, G, H 5-12: supernatants of induced PBMCs from the other blood donor.

The results in FIG. 1 demonstrated that the artificial CpG-containing single-stranded oligodeoxynucleotides DVAX-1, DVAX-3, DVAX-4, DVAX-5 and DVAX-6 (SEQ ID NOs: 1-5) could stimulate human PBMC to produce antiviral substances, which provide significant protection for Vero cells against the attack of virus. The artificial CpG-containing single-stranded oligodeoxynucleotides DVAX-1, DVAX-3, DVAX-4, DVAX-5 and DVAX-6 (SEQ ID NO: 1-5) were effective for the treatment and prevention of human respiratory infectious diseases such as influenza caused by influenza virus.

Example 3

Antiviral Activity of Artificial CpG-Containing Single-Stranded Oligodeoxynucleotide to Single-Stranded Positive Strand RNA Virus-SARS Virus 1. Separation of PBMCs
   Same as Example 2.

2. Obtaining the Culture Supernatant of Human PBMCs Stimulated by CpG ODN (DVAX-1)

Human PBMCs in RPMI 1640 complete medium supplemented with 10% FCS was seeded into 12-well plate (2 ml/well) and the concentration of cell was $4 \times 10^6$ cells/ml. CpG ODN (DVAX-1) sterilized by filtration was added to final concentrations of 25 μg/ml, 12.5 μg/ml, 6.25 μg/ml and 3.13 μg/ml, respectively. Culture without CpG ODN was used as control. After incubation at 37° C. under 5% $CO_2$ for 48 hours, supernatants were collected and stored at −20° C. until use.

3. Determination of Antiviral Activity of Artificial CpG-Containing Single-Stranded Oligodeoxynucleotide to SARS Virus This experiment was carried out at Institute of Virus Control and Prevention in the Chinese Center for Disease Control and Prevention.

African green monkey kidney passage cells (VERO E6, provided by Institute of Virus Control and Prevention in the Chinese Center for Disease Control and Prevention) were seeded into 96-cell plate with a cell concentration of $4\times10^5$/ml. After incubation at 37° C. in 5% $CO_2$ for 24 hours, culture media were discarded. 100TCCID50 SARS-CoV Sino-5 strain [(#4 serum sample from acute SARS patient): provided by Youanmen Hospital of Beijing, identified by and stored at Institute of Virus Control and Prevention in the Chinese Center for Disease Control and Prevention] was added and incubated at 37° C. in 5% $CO_2$ for 2 hours. Viral solution was discarded and the culture supernatant of human PBMCs stimulated by CpG ODN (DVAX-1) was added in duplicate, 100 μl/well. Recombinant human interferon α2b (Yuancein, positive control drug, 1,000,000 IU/vial, China drug authorization No: S19990013, Lot No: 000503A, manufactured by Beijing Yuance Pharmaceutical Corporation Limited) and medium controls, cell control and virus control were cultured at 37° C. in 5% $CO_2$ for 6 days. Cytopathic effect (CPE) was observed under microscope, wherein "+" denoted pathological change in 25% of cells, "++" denoted pathological change in 26-50% of cells, "+++" denoted pathological change in 51-75% of cells and "++++" denoted pathological change in 76-100% of cells. After study of CPE, each well was added with 100 μl of 0.5% crystal violet staining solution (0.5 g crystal violet, 0.85 g NaCl, dissolved in a mixture of 50 ml absolute ethyl ether, 3 ml formaldehyde and 47 ml distilled water) and incubated at 37° C. in 5% $CO_2$ for 15 min. After wash with flowing water, each well was added 100 μl destaining solution (50 ml ethylene glycol monomethyl ether, 50 ml distilled water). After shaking at room temperature for 2 hours, ELISA detector was used to read OD values at 492 nm.

Result Analysis:

The results of CPE method demonstrated that:
the culture supernatant of human PBMC which was stimulated by 25 μg/ml CpG ODN (DVAX-1) for 48 hours and diluted at 1:160, could effectively inhibit the SARS-CoV Sino-5 strain;
the culture supernatant of human PBMC which was stimulated by 12.5 μg/ml CpG ODN (DVAX-1) for 48 hours and diluted at 1:80, could effectively inhibit the SARS-CoV Sino-5 strain;
the culture supernatant of human PBMC which was stimulated by 6.25 μg/ml CpG ODN (DVAX-1) for 48 hours and diluted at 1:40, could effectively inhibit the SARS-CoV Sino-5 strain;
recombinant human interferon α2b which was diluted to above 50,000 IU, could effectively inhibit the SARS-CoV Sino-5 strain; and
the culture supernatant without CpG ODN had no inhibitory effect on the SARS-CoV Sino-5 strain.

The results of crystal violet staining demonstrated that:
the culture supernatant of human PBMC which was stimulated by 25 μg/ml CpG ODN (DVAX-1) for 48 hours and diluted at 1:80, could effectively inhibit the SARS-CoV Sino-5 strain;
the culture supernatant of human PBMC which was stimulated by 12.5 μg/ml CpG ODN (DVAX-1) for 48 hours and diluted at 1:80, could effectively inhibit the SARS-CoV Sino-5 strain;
the culture supernatant of human PBMC which was stimulated by 6.25 μg/ml CpG ODN (DVAX-1) for 48 hours and diluted at 1:20, could effectively inhibit the SARS-CoV Sino-5 strain;
recombinant human interferon α2b which was diluted to above 50,000 IU, could effectively inhibit the SARS-CoV Sino-5 strain; and
the culture supernatant without CpG ODN had no inhibitory effect on the SARS-CoV Sino-5 strain.

In view of above, human PBMC stimulated by CpG ODN (DVAX-1) could be induced to produce antiviral substances against single-stranded positive strand RNA virus—SARS virus in supernatant, and CpG ODN (DVAX-1) could stimulate cell to produce antiviral substance to protect from the infection of single-stranded positive strand RNA virus—SARS virus.

Example 4

Antiviral Activity of Artificial CpG-Containing Single-Stranded Oligodeoxynucleotide to Single-Stranded Positive Strand RNA Virus-Dengue Virus 1. Separation of PBMCs
   Same as Example 2.

2. Obtaining the Culture Supernatant of Human PBMCs Stimulated by CpG ODN (DVAX-1)
   Same as Example 3.

3. Determination of Antiviral Activity of Artificial CpG-Containing Single-Stranded Oligodeoxynucleotide to Dengue Virus 200 μl VERO E6 cell suspension was seeded into 96-well plate, and cell concentration was $4\times10^5$/ml. After inoculation at 37° C. in 5% $CO_2$ for 24 hours, culture media was discarded. 100TCCID50 dengue virus (D2V strain NGC, produced by C6/36 insect cell (ATCC)) was added and incubated at 37° C. in 5% $CO_2$ for 2 hours. Viral solution was discarded and the culture supernatant of human PBMCs stimulated by CpG ODN (DVAX-1) was added in triplicate, 100 μl/well. Cell control and virus control were cultured at 37° C. in 5% $CO_2$ for 8 days. Cytopathic effect (CPE) was observed under microscope, wherein "+" denoted pathological change in 25% of cells, "++" denoted pathological change in 26-50% of cells, "+++" denoted pathological change in 51-75% of cells and "++++" denoted pathological change in 76-100% of cells.

The results of CPE method demonstrated that:
the culture supernatant of human PBMC which was stimulated by 25 μg/ml CpG ODN (DVAX-1) for 48 hours and diluted at 1:80, could effectively inhibit dengue virus;
the culture supernatant of human PBMC which was stimulated by 12.5 μg/ml CpG ODN (DVAX-1) for 48 hours and diluted at 1:80, could effectively inhibit dengue virus;
the culture supernatant of human PBMC which was stimulated by 6.25 μg/ml CpG ODN (DVAX-1) for 48 hours and diluted at 1:40, could effectively inhibit dengue virus; and
the culture supernatant without CpG ODN had no inhibitory effect on dengue virus. CPE occurred in 100% cells of virus control.

In view of above, human PBMC stimulated by CpG ODN (DVAX-1) could be induced to produce antiviral substances against single-stranded positive strand RNA virus—dengue virus in supernatant, and CpG ODN (DVAX-1) could stimulate cell to produce antiviral substance to protect from the infection of single-stranded positive strand RNA virus—dengue virus.

Example 5

Antiviral Activity of Artificial CpG-Containing Single-Stranded Oligodeoxynucleotide to Single-Stranded Positive Strand RNA Virus—Japanese Encephalitis Virus 1. Separation of PBMCs
Same as Example 2.

2. Obtaining the Culture Supernatant of Human PBMCs Stimulated by CpG ODN (DVAX-1)
Same as Example 3.

3. Determination of Antiviral Activity of Artificial CpG-Containing Single-Stranded Oligodeoxynucleotide to Japanese Encephalitis Virus 200 μl BHK-21 cell suspension (purchased from Mongolia Biopharmaceutical Factory) was seeded into 96-well plate, and cell concentration was $4 \times 10^5$/ml. After inoculation at 37° C. in 5% $CO_2$ for 24 hours, culture media was discarded. 100TCCID50 Japanese encephalitis virus (provided by Changchun Institute of Biological Products) and incubated at 37° C. in 5% $CO_2$ for 2 hours. Viral solution was discarded and the culture supernatant of human PBMCs stimulated by CpG ODN (DVAX-1) was added in triplicate, 100 μl/well. Cell control and virus control were cultured at 37° C. in 5% $CO_2$ for 4 days. Cytopathic effect (CPE) was observed under microscope, wherein "+" denoted pathological change in 25% of cells, "++" denoted pathological change in 26-50% of cells, "+++" denoted pathological change in 51-75% of cells and "++++" denoted pathological change in 76-100% of cells.

The results of CPE method demonstrated that:

the culture supernatant of human PBMC which was stimulated by 25 μg/ml CpG ODN (DVAX-1) for 48 hours and diluted at 1:160, could effectively inhibit Japanese encephalitis virus;

the culture supernatant of human PBMC which was stimulated by 12.5 μg/ml CpG ODN (DVAX-1) for 48 hours and diluted at 1:80, could effectively inhibit Japanese encephalitis virus;

the culture supernatant of human PBMC which was stimulated by 6.25 μg/ml CpG ODN (DVAX-1) for 48 hours and diluted at 1:40, could effectively inhibit Japanese encephalitis virus; and the culture supernatant without CpG ODN had no inhibitory effect on Japanese encephalitis virus. CPE occurred in 100% cells of virus control.

In view of above, human PBMC stimulated by CpG ODN (DVAX-1) could be induced to produce antiviral substances against single-stranded positive strand RNA virus—Japanese encephalitis virus in supernatant, and CpG ODN (DVAX-1) could stimulate cell to produce antiviral substance to protect from the infection of single-stranded positive strand RNA virus—Japanese encephalitis virus.

What is claimed is:

1. An artificial CpG-containing single-stranded oligodeoxynucleotide, which consists of a single-stranded oligonucleotide DNA molecule containing one or more CpG(s) which has a sequence as defined by SEQ ID NO: 1, SEQ ID NO: 2, SEQ ID NO: 3, SEQ ID NO: 4 or SEQ ID NO: 5.

2. The oligonucleotide according to claim 1, which has a function of inducing the production of antiviral substances from cell.

3. The oligonucleotide according to claim 2, wherein the antiviral substances are against a single-stranded positive strand RNA virus or influenza virus.

4. The oligonucleotide according to claim 3, wherein said single-stranded positive strand RNA virus is a variant of coronavirus or flaviviridae virus.

5. The oligonucleotide according to claim 4, wherein said variant of coronavirus is SARS virus.

6. The oligonucleotide according to claim 4, wherein said flaviviridae virus is hepatitis C virus, dengue virus or Japanese encephalitis virus.

7. The oligonucleotide according to claim 1, which has a non-sulfurized, partially sulfurized or completely sulfurized phosphodiester bond.

8. A composition comprising the oligonucleotide according to claim 1.

9. The composition according to claim 8, further comprising other antiviral drugs or vaccines.

10. A method for inducing the production of antiviral substances from cell comprising treating said cell with the oligonucleotide of claim 1.

11. The method of claim 10, wherein the antiviral substances are against single-stranded positive strand RNA virus or influenza virus.

12. The method of claim 11, wherein said single-stranded positive strand RNA virus is a variant of coronavirus or flaviviridae virus.

13. The method of claim 12, wherein said variant of coronavirus is SARS virus.

14. The method of claim 12, wherein said flaviviridae virus is hepatitis C virus, dengue virus or Japanese encephalitis virus.

* * * * *

UNITED STATES PATENT AND TRADEMARK OFFICE
CERTIFICATE OF CORRECTION

| | |
|---|---|
| PATENT NO. | : 7,491,706 B2 |
| APPLICATION NO. | : 10/565718 |
| DATED | : February 17, 2009 |
| INVENTOR(S) | : Yu et al. |

It is certified that error appears in the above-identified patent and that said Letters Patent is hereby corrected as shown below:

Column 6, Line 7, "$Na_2HPO_4.H_2O$" should be changed to --$Na_2HPO_4 \cdot H_2O$--

Column 7-8, Line 12, Table 1, "6.25 µ/ml" should be changed to --6.25 µg/ml--

Signed and Sealed this

Second Day of June, 2009

JOHN DOLL
*Acting Director of the United States Patent and Trademark Office*